United States Patent
Shiloach et al.

(10) Patent No.: US 10,702,456 B2
(45) Date of Patent: Jul. 7, 2020

(54) IN-SITU PROCESS FOR MAKING A SMALL PARTICLE NARROW DISTRIBUTION FATTY ACYL ISETHIONATE IN OIL COMPOSITION

(71) Applicant: Conopco, Inc., Englewood Cliffs, NJ (US)

(72) Inventors: Anat Shiloach, Trumbull, CT (US); John Robert Winters, Dumont, NJ (US); Badreddine Ahtchi-Ali, Montebello, NY (US)

(73) Assignee: CONOPCO, INC., Englewood Cliffs, NJ (US)

( * ) Notice: Subject to any disclaimer, the term of this patent is extended or adjusted under 35 U.S.C. 154(b) by 250 days.

(21) Appl. No.: 15/743,695

(22) PCT Filed: Jul. 8, 2016

(86) PCT No.: PCT/EP2016/066370
§ 371 (c)(1),
(2) Date: Jan. 11, 2018

(87) PCT Pub. No.: WO2017/009267
PCT Pub. Date: Jan. 19, 2017

(65) Prior Publication Data
US 2018/0200160 A1    Jul. 19, 2018

(30) Foreign Application Priority Data

Jul. 16, 2015   (EP) ................................... 15177092
Jul. 16, 2015   (EP) ................................... 15177102

(51) Int. Cl.
| | | |
|---|---|---|
| *A61K 8/04* | (2006.01) | |
| *A61K 8/27* | (2006.01) | |
| *A61K 8/31* | (2006.01) | |
| *A61K 8/46* | (2006.01) | |
| *A61Q 19/10* | (2006.01) | |
| *A61K 8/92* | (2006.01) | |
| *C11C 3/00* | (2006.01) | |

(52) U.S. Cl.
CPC .............. *A61K 8/044* (2013.01); *A61K 8/046* (2013.01); *A61K 8/27* (2013.01); *A61K 8/31* (2013.01); *A61K 8/466* (2013.01); *A61K 8/922* (2013.01); *A61Q 19/10* (2013.01); *A61K 2800/31* (2013.01); *A61K 2800/412* (2013.01); *C11C 3/003* (2013.01)

(58) Field of Classification Search
CPC . A61K 8/044; A61K 8/27; A61K 8/31; A61K 8/466; A61K 8/922; A61K 8/046; A61K 2800/31; A61K 2800/412; A61Q 19/10; C11C 3/003
See application file for complete search history.

(56) References Cited

U.S. PATENT DOCUMENTS

| | | | |
|---|---|---|---|
| 3,029,264 A | 4/1962 | van Alphen et al. | |
| 4,673,526 A | 6/1987 | Zabotto et al. | |
| 6,069,262 A | 5/2000 | Walele et al. | |
| 6,524,594 B1 | 2/2003 | Santora et al. | |
| 6,620,773 B1 | 9/2003 | Stork et al. | |
| 8,063,005 B2 | 11/2011 | Kalidindi | |
| 8,111,824 B2 | 2/2012 | Gaggl et al. | |
| 2004/0136942 A1 | 7/2004 | Yamazaki | |
| 2005/0158351 A1 | 7/2005 | Soliman et al. | |
| 2006/0089279 A1* | 4/2006 | Brennan ................ | A61K 8/361 510/141 |
| 2008/0153727 A1 | 6/2008 | Tsaur et al. | |
| 2008/0153729 A1 | 6/2008 | Tsaur et al. | |
| 2008/0153730 A1 | 6/2008 | Tsaur | |
| 2010/0210500 A1 | 8/2010 | Liu et al. | |
| 2012/0094884 A1 | 4/2012 | Liu et al. | |
| 2012/0094885 A1 | 4/2012 | Liu et al. | |
| 2014/0050347 A1 | 2/2014 | Tsai | |
| 2014/0155309 A1 | 6/2014 | Cotrell et al. | |

FOREIGN PATENT DOCUMENTS

| | | |
|---|---|---|
| CN | 103797107 | 5/2014 |
| EP | 0214865 | 3/1987 |
| EP | 0585071 | 3/1994 |
| WO | WO9842658 | 10/1998 |
| WO | WO9904751 | 2/1999 |
| WO | WO0021492 | 4/2000 |
| WO | WO02079717 | 10/2002 |
| WO | WO03051319 | 6/2003 |
| WO | WO2015014604 | 2/2015 |
| WO | WO2015014667 | 2/2015 |

OTHER PUBLICATIONS

Search Report in EP15177092; dated Dec. 16, 2015.
Written Opinion in EP15177092; dated Dec. 16, 2015.
Delivering Value Through Versatility, INEOS Oligomers Indopol Polybutene Product Bulletin, Nov. 30, 2009, pp. 1-34; XP055147638.
IPRP2 in PCTEP2016066370, Sep. 22, 2017.
Search Report and Written Opinion in EP15177102, dated Dec. 2, 2015.
Search Report and Written Opinion in PCTEP2016066370, dated Sep. 19, 2016.
Written Opinion 2 in PCTEP2016066370, dated May 26, 2017.

* cited by examiner

*Primary Examiner* — Robert S Jones
(74) *Attorney, Agent, or Firm* — Krista A. Kostiew

(57) ABSTRACT

The invention relates to novel compositions and novel in-situ process for making small average particle size, narrow distribution FAI in oil. The process comprises preparing FAI; separately optionally heating oil; adding oil to FAI in a molten state; heating to defined temperature; and cooling the heated mixture at a defined, controlled rate which ensures proper size and distribution are met.

14 Claims, No Drawings

IN-SITU PROCESS FOR MAKING A SMALL PARTICLE NARROW DISTRIBUTION FATTY ACYL ISETHIONATE IN OIL COMPOSITION

FIELD OF THE INVENTION

The invention relates to so-called oil continuous compositions (OCC) and to pre-mixes (which may also be referred to as oil-continuous) used in the preparation of the final composition. OCCs are non-aqueous suspensions of fine solid surfactant particles (e.g., acyl isethionate, glycinate, betaine) in a continuous oil phase. The continuous, non-aqueous oil phase may comprise mineral oils, natural oils or polyols, and may serve both as carrier (e.g., for cleansing surfactant) and as skin benefit agent (e.g., the oil itself) which can deliver high levels of deposition. The OCC are typically foamable personal care compositions including, for example, cleansing compositions, make-up removers, shaving compositions, and other lather-off compositions for skin and/or hair treatment, The invention further relates to an in-situ process for making these compositions.

BACKGROUND OF THE INVENTION

Many foamable personal care compositions are water-based liquids that include one or more synthetic cleansing, i.e., detersive, surfactants commonly known as "syndet" and herein alternatively referred to as "synthetic surfactant" or "cleansing surfactant". The compositions are commonly oil-in-water emulsions in which a surfactant-containing aqueous phase is combined with an oil phase and other composition ingredients, e.g., volatiles. Creating concentrates (used, for example, as pre-mixes) with conventional water-based liquid detergents can be problematic in that the reduced amount of water in a concentrate can give rise to products that are prone to gel formation or crystallization and, as a result, such concentrates are too viscous to be easily applied or diluted, OCCs are desirably foamable fluid compositions having a continuous oil phase, and which offer potential advantages over conventional water-based compositions in one or more areas, e.g., processing, concentrate formation. As discussed in WO 2015/014604 to Tsaur et al., various oil-based personal care compositions are disclosed. These include U.S. Pat. No. 4,673,526 to Zabotto; U.S. Pat. No. 8,063,005 to Kalidindi; U.S. Pat. No. 6,620,773 to Stork; U.S. Pat. No. 6,524,594 to Santora; and U.S. Publication No. 2005/0158351 A1 to Subramanian.

As noted in WO 2015/014604 to Tsaur, formulating continuous oil phase compositions with desirable phase stability has been problematic. As a disperse phase in oil, solid surfactant tends to separate over time, which can form a layer of particles at the bottom and oil at the top. This tendency increases when larger or heavier particles are used. Conventional stabilization routes, e.g., use of viscosity modifiers and thickeners, can interfere with surfactant release in use, which in turn can affect foam formation and lathering. WO 2015/014604 to Tsaur addresses these issues by using relatively small amounts of fatty acid soap crystals to stabilize synthetic surfactant in the oil phase. At the pH ranges used in compositions of our invention (e.g., 3.0 to 6.5, preferably 4.0 to 6.0) such crystals do not form and indeed compositions of our invention are free of the fatty acid soap crystal defined in the Tsaur application. Rather, compositions of our invention are prepared by a novel process involving low shear rates and a slow cooling rate.

The present invention relates to non-aqueous oil continuous pre-mix compositions comprising fatty acyl isethionate surfactants (e.g., cocoyl isethionate), which pre-mixes may be used in a final OCC (in theory, the pre-mix can be used as "final" OCC if desired) or which pre-mixes may be used as ingredients in formulation of other compositions. The pre-mix compositions are desirable because compositions comprising fatty acyl isethionate surfactants lather well, are mild to the skin and have good emollient properties.

Preparation of OCCs containing fatty acyl isethionate surfactants (when these surfactants are produced by the direct esterification of fatty acid and isethionate, they are commonly referred to as "DEFI" surfactants) can be problematic. Specifically, it is important to obtain fatty acyl isethionate (FAI) particles having an average particle size of 100 microns or below, preferably less than 75 microns, more preferably less than 50 microns. Typically, such small size particles are not perceived as "gritty" by the consumer. It is also believed that the small particles are more readily pumpable and thus make the pre-mix easier to incorporate into a final composition or into containers during processing.

One way to ensure particles having a small average particle size are obtained is through in-line wet milling. This process comprises milling larger size FAI particles which have been combined with oil using specialized ultra high shear equipment (up to 100,000 $s^{-1}$) designed to reduce average particle size below 100 microns. During production of OCC, this may then be followed by subsequent addition of other solid surfactants (e.g., betaine and/or glycinate powders). Polymer and soap are typically further added as structurants to the main mixer. The wet milling process is energy intensive (high shear transferred to product), leading to product temperature increase and requiring product cooling. The process can be expensive as well as it requires introducing an in-line wet mill and a heat exchanger to the mixer design. Further, it is difficult to control the particle size distribution (e.g., particle span) when using wet milling process.

Applicants have now found that small average particle size FAI (having average particle size of 100 microns or less, also having a narrow particle size distribution) can be formed in a FAI/oil premix (to be used in the final OCC) using a specific in-situ process where (1) heated oil and molten FAI (obtained, for example, from the directly esterified fatty acyl isethionate or "DEFI", formed at end of a DEFI reaction) are mixed; (2) the mixture is heated to ensure liquid phase formation; and (3) the mixture is cooled in a controlled manner (e.g., 0.5 to 5° C. per minute) to ensure that surfactant particles of average particle size of 100 microns or less are formed. Using a controlled cooling process, it is possible to make small average particle size particles at relatively low shear rate (e.g., 10 to under 1000 $sec^{-1}$; shear rate is estimated based on the physical dimensions of the reactor/homogenizer and rotation in revolutions per minute or RPM; shear rates of our invention were estimated at about 95-100 $sec^{-1}$ at 350 RPM). The shear rate during step c) and/or d) is 10 to 1000 $sec^{-1}$.

In addition, in the process of our invention, water is driven off during the DEFI reaction (high temperature reaction occurring at 200 to 245° C.) and no water is re-added as this would be unnecessary and inefficient. Although there is a small amount of water that comes in with the initial raw materials, preferably the final composition contains less than 2%, or 1% or less, or 0.5% or less (0 to 0.5% by wt.) water.

The present invention is directed to the novel small average particle size, narrow particle distribution FAI in oil compositions themselves. It is further directed to a novel process for obtaining the novel compositions.

The process of the invention for forming the pre-mix relates typically to combination of FAI and oil, although optional structurants (e.g., soap) and emulsifiers may be part of the process for forming the pre-mix. The pre-mix (containing FAI and oil, optional structurant and optional emulsifier) can be later combined with other ingredients to form final OCC. This intermediate pre-mix is in effect a raw material which can be made, and then stored and used as needed to make the "final" OCC (as noted, if desired the intermediate pre-mix may be the final OCC) or to make other cleaning formulations. It is noted that, if FAI is made by DEFT process, the pre-mix can comprise both the FAI formed from the reaction as well as unreacted fatty acid, unreacted isethionate salt (e.g., sodium isethionate), catalyst (if employed), and any trace impurities which might be present in the raw materials.

Processes for making fatty acid esters of salts of isethionate (e.g., by reacting fatty acid with sodium salt of hydroxyl alkyl sulfonates to form, for example, sodium cocoyl isethionate or "SCI") are not new (the direct esterification of fatty acid and the sodium salt are, as noted, what is referred to as "DEFT" reaction). U.S. Pat. No. 6,069,262 to Walele et al., WO 98/42658, U.S. Pat. No. 3,029,264 to Voorburg and many other references disclose such processes for example.

None of the references relating to formation of salt of acyl isethionate disclose in-situ processes wherein, at the end of a process for making FAI (e.g., DEFI process), molten FAI and oil (optionally heated) are combined, the mixture is further heated to ensure liquid phase formation, and this mixture is then cooled in a controlled manner (e.g., defined rate of temperature drop per minute) to obtain FAI crystals which have an average particle size of 100 microns or less, and further have a narrow particle size distribution (e.g., span, as defined below, of less than 4.5, preferably less than 4, more preferably less than 3). Compositions made by such process are also not disclosed.

Many references disclose compositions containing oils or compositions containing fatty acyl isethionate or compositions containing both but, again, none of these disclose a specific in-situ process for making a premix comprising FAI and oil which process involves cooling FAI (plus any unreacted fatty acid, unreacted salt of isethionate, catalysts (if employed), and trace impurities, if any, which may be the by-product of the invention) and oil (in addition to any optional structurant and/or emulsifier) which have been combined as noted above in a controlled manner to ensure small average particle size FAI particles in oil, wherein the particles further have a narrow particle size distribution (defined by span); and further wherein reaction is at low shear (<1000 $sec^{-1}$) and no water is added during the reaction. Preferably, the final composition of our invention have less than 2%, e.g., 0 to less than 2% by wt. water.

WO 2002/079717 to Merz, for example, appears to disclose liposome forming aqueous bath which may contain oil (claim 5) and isethionate (claim 6) but the controlled cooling, low shear process of the invention and formation of small average particle size, narrow particle distribution FAI does not appear to be disclosed.

U.S. Pat. No. 8,111,824 to Dasgupta et al.; U.S. 2012/0094884, U.S. 2012/0094885, and U.S. 2010/0210500 all to Liu; and U.S. 2008/0153727, U.S. 2008/0513729 and U.S. 2008/0153730, all to Tsaur et al., all disclose compositions with DEFI and oils in the composition. There is no disclosure of a FAI in oil premix, or of a specific process for making such premix and ensuring in-situ formation of small average particle size FAI further having narrow particle size distribution.

Similarly, US 2004/0136942 to Yamazaki, WO 03/051319 to Beirsdorf and WO 00/21492 to Johnson and Johnson disclose compositions which may have DEFI and oils, but there is no teaching of specific FAI-in-oil premix concentrates or processes to form these and ensure formation of small average particle size FAI further having narrow particle size distribution.

WO 99/04751 to Puvvada et al. (Unilever) discloses compositions where the level of oil-emollient is equal to or in excess of level of surfactant. First, no FAI is even specified.

Further, there is again no disclosure of the specific process of our invention or of the compositions of our invention.

EP0585071 to Hoechst discloses a process for making sodium acylisethionate which comprises directly esterifying fatty acid and hydroxyalkanesulfonic acid at a temperature of about 180°-240° C., adding paraffin to the reaction mixture, distilling excess fatty acid, cooling preferably to below 180° C., and adding more fatty acid and anhydrous metal alkali salts. No information is given about rate of cooling and, from Example 1, it is seen that at about 100° C., ice water is added and there is rapid cooling. This differs significantly from our process where (1) there is a constant and controlled rate of cooling and (2) where excess cooling leads to significantly higher particle size distribution (see our Example 3). Average particle size and particle distribution, and the processing effect on these parameters is unrecognized and unmentioned in the reference.

WO 2015/014604 noted above discloses use of fatty acid soap crystals to stabilize surfactant. At the pH levels used in compositions of our invention, such fatty acid soap crystals do not form.

In related WO 2015/014667, stabilization is achieved either by using pre-aggregated solid surfactants and/or solid surfactant particles that are aggregated in situ by addition of water. Particles of the invention are not pre-aggregated, nor is water added in our DEFT reaction since such would add additional complexity and inefficiency.

US 2014/155309 relates to solid personal care bars. The compositions utilize synthetic waxes which are solid at room temperature (e.g., 20-25° C.). Oils used in the compositions of our invention are preferably liquid at room temperature.

BRIEF DESCRIPTION OF THE INVENTION

Unexpectedly, applicants have now found novel non-aqueous oil continuous pre-mixes (using precisely controlled cooling) comprising FAI particles (preferably prepared via a DEFT process, especially a low-shear DEFT process) which have an average particle size of 100 microns or below, preferably 75 microns or below, more preferably 0.1 to 50 microns. Even more preferably, average particle size is 1 to 40 microns. Preferably, the particle size span (which is a measure of the distribution of particles) is less than 4.5, preferably less than 4. The compositions are free of fatty acid soap crystals and particles are neither pre-aggregated or aggregated in-situ by addition of water.

Compositions of the invention are made by a novel process. Preferably, the composition comprises 25 to 90% oil and 10 to 60% FAI, more preferably 40 to 90% or 30 to 85% or even more preferably 50 to 85% or even 50 to 80% oil and 15-50% FAI. The process for making said novel compositions is an in-situ process for formation of FAI particles having an average particle size of 100 microns or less, preferably 75 microns or less; and a narrow particle size distribution (span of less than 4.5), wherein said process comprises:

a) preparing FAI in a reactor by reacting (optionally in the presence of a catalyst; catalysts, if used, may include multivalent metal ion salts, strong acids, acidified zinc oxide, soluble zinc salts, and combinations thereof; zinc oxide is a preferred catalyst):

HOR'SO$_3$M where R' is divalent hydrocarbon radical having 2-4 carbons and M is an alkali metal cation, with organic acid RCOOH, where R is monovalent aliphatic radical having 7 to 24 carbons (e.g., C$_7$ to C$_{24}$ fatty acid, preferably C$_8$ to C$_{18}$ fatty acid; C$_{12}$ is a preferred fatty acid)

to produce RCOOR'SO$_3$M (R, R' and M are defined as above)

wherein reactants are first combined at a temperature of about 20-25° C. (room temperature) and heated to about 200-245° C.;

(As noted previously, the reaction will not typically go to 100% completion so that there will be a mix of FAI and unreacted fatty acid and unreacted isethionate salt, as well as other catalyst, if used, and trace impurities, if any).

b) optionally heating oil in a separate reactor at a temperature of 80° to 130° C. (this is done to avoid excessively reducing the batch temperature upon addition of oil);

c) adding said oil to the FAI while FAI is still in molten state (typically at temperature of 200-245° C.);

d) continuing to heat the mixture of FAI and oil at temperature of 200° to 245° C. to form a liquid phase mixture of FAI, unreacted fatty acid, unreacted isethionate, catalyst (e.g., ZnO), if used, trace impurities, if any, and oil; and e) cooling the mixture at 0.5 to 5° C., preferably 0.5 to 3° C., more preferably 0.5 to 2° C. per minute to ensure a premix where the average particle size is 100 microns or less and particle size span is less than 4.5.

It is the controlled rate of cooling of pre-mix which is believed to form small average particle FAI in the oil wherein FAI has narrow particle size distribution having a span of less than 4.5. It is preferred further that the temperature drop be consistent throughout the reactor.

The mixture is cooled to below the solidification temperature of the FAI, typically to a temperature below 170° C. Preferably, it is cooled to a temperature of 25° to 70° C.

The pH of compositions of the invention (which, without being bound by theory, is believed associated with absence of fatty acid soap crystals) is preferably 3.0 to 6.5, more preferably 4.0 to 6.0. pH may be slightly higher but not so high as will lead for formation of fatty acid soap crystals.

Oils used in the invention typically are liquid at room temperature. Melting points of such oils is typically 30° C. and below, preferably, 25° C. and below, more preferably, having upper range of 10 to 20° C. (petrolatum typically has MP of 35° to 37° C.). Preferably, the oil comprises mineral oil. Preferably, oil (all oil of invention including mineral oil) is used in an amount of at least 25% (e.g., 25 to 90% by wt.) of the composition. In one embodiment, mineral oil is used and preferably it comprises 25% to 70% of the composition.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about."

As used throughout, ranges are used as shorthand for describing each and every value that is within the range. Any value within the range can be selected as terminus of the range. The use of and/or indicates that any one from the list can be chosen individually or any combination from the list can be chosen.

For the avoidance of doubt, the word "comprising" is intended to mean "including" but not necessarily "consisting of" or "composed of." In other words, the listed steps or options need not be exhaustive.

Unless indicated otherwise, all percentages for amount or amounts of ingredients used are to be understood to be percentages by weight based on the active weights of the material in the total weight of the composition where total is 100%.

The disclosure of the invention as found herein is to be considered to cover all embodiments as found in the claims as being multiply dependent upon each other irrespective of the fact that claims may be found without multiple dependency or redundancy.

The present invention relates to FAI in oil compositions and to process for making such composition. The compositions are made by an in-situ process for making a FAI in oil pre-mix wherein FAI particles have an average particle size of 100 microns or less, preferably 75 microns or less, more preferably 0.1 to 50 microns, even more preferably 0.1 to 40 microns; and particle size span (measure of distribution) of less than 4.5. These particles are thus not perceived as "gritty" within the pre-mix or within the final OCC or any other formulation in which pre-mix is used. While not wishing to be bound to theory, it is believed the small particles also may help make the pre-mix more readily pumpable and thus easier to incorporate into any final composition in which it might be used.

The in-situ process for making novel compositions of our invention is used instead of processes involving wet milling and, because the higher shear used during wet milling is avoided, no additional milling equipment or heat exchanger (to control temperature rise from the wet milling) are needed. Specifically, the low shear used to make compositions of the invention (less than 1000 sec$^{-1}$, specifically shear of 95-100 sec$^{-1}$ at RPM of 350) is an order or two orders of magnitude less than shear rates used in typical high shear homogenizers.

Further advantage is found in that there is no need to handle FAI solids if using the pre-mix in a full formulation. That is, if solid particles are added, the solids would have to be transferred efficiently to a batch tank. This in turn can create dust or safety hazards. When formed as a liquid, as per the invention, the dust hazards are avoided and, as noted, it is believed the liquids can be more readily pumped.

When made by wet-milling, the particle in oil mix is typically more viscous at the same level of solids. This makes wet-milled slurries more paste-like and harder to pump. While not wishing to be bound by theory, this could be due to water content, or to the particle size distribution (larger span, e.g., greater than 4.5).

Remarkably and unexpectedly, applicants have found that, by using a "controlled cooling" rate step whereby oil and FAI (optionally, structurant and/or emulsifier can be in pre-mix) are first mixed while FAI is in a molten state and this premix is then cooled in small intervals (e.g., 0.5 to 5° C. per minute), the final product (compositions of the invention) comprises FAI surfactant in oil wherein small average particle size FAI is formed and there is a narrow particle size distribution (defined by span). Without wishing to be bound by theory, it is believed that slow interval, even rate cooling of the molten mixture allows one to avoid rapid cool temperature shock and permits solidification of the FAI particle in a way which allows small average size particles with narrow particle size span to form in oil. This provides both processing (pumpability) and product (less grittiness) advantages.

The compositions are free of fatty acid soap crystals; and the particles are neither pre-aggregated nor aggregated in-situ by the addition of water. Preferably, final compositions comprise less than 2% water.

More specifically, the invention provides a novel composition having small average size particles of narrow distribution. The compositions are made by an in-situ process for forming FAI-in-oil mixture comprising:

a) preparing FAI in a reactor by reacting (optionally in presence of a catalyst):
   $HOR'SO_3M$,
   where R' is divalent hydrocarbon radical having 2-4 carbons and M is an alkali metal cation,
   with organic acid RCOOH,
   where R is monovalent aliphatic radical having 7 to 24 carbons (preferably $C_8$ to $C_{18}$, more preferably $C_{12}$ to $C_{14}$, more preferably $C_{12}$)
   to produce $RCOOR'SO_3M$
   (R, R' and M are defined as above)
   wherein reactants are first combined at a temperature of 20-25° C. (It should be understood that the reactants can be combined, if desired, at a temperature higher than room temperature and heating).

b) optionally heating oil in a separate reactor at a temperature of 80° to 130° C.;

c) adding said oil to the FAI while FAI is still in molten state (200-245° C.);

d) continuing to heat the mixture of FAI and oil at temperature of 200° C. to 245° C. to form a liquid phase mixture of FAI, unreacted fatty acids, unreacted isethionate, catalyst, if used, trace impurities, if any, and oil; and e) cooling the mixture at 0.5 to 5° C., preferably 0.5° to 3° C. per minute to ensure premix where average particle size is 100 microns or less and particle span is less than 4.5. Preferably, difference in cooling rate between any two portions of the reactor will not exceed 3° C./minute. That is, the cooling rate should be approximately even throughout the reactor. This ensures the average particle size and span stay within defined parameters.

The mixture is cooled to a temperature below the solidification temperature of FAI, typically to below 170° C.; preferably 25° C. to 70° C.

The compositions have pH of 3.0 to 6.5, preferably 4.0 to 6.0; this pH is believed to ensure the compositions are free of fatty acid soap crystals. Preferably, the process comprises a pH adjustment, to result in a pH of the resulting composition of between 3.0 and 6.5, preferably 4.0 to 6.0.

The compositions of the invention are produced as an extension of the fatty acyl isethionate manufacturing process, which process involves low-shear mixing with no additional process equipment required. Homogenization, by contrast, is shear-intensive and requires the use of additional process equipment, which again, our process does not require.

Shear rate for a homogneizer can be calculated as:

$$\text{Shear rate}(sec^{-1}) = \text{Rotor tip speed}(M/s)/\text{Gap between rotor and stator}(M).$$

Applying the same calculation to the process reactor used to make our compositions, the shear rate can be estimated as:

$$\text{Shear rate}(sec^{-1}) = \text{Impeller speed}(M/s)/\text{Gap between impeller and reactor wall}(M).$$

For comparison,

Approximate calculated shear rate for a typical homogenizer (Silverson L5M-A laboratory homogenizer at 5,000 RPM)=41,495 $sec^{-1}$.

Approximate calculated shear rate in reactor (DEFI pilot plant reactor at 350 RPM)=98 $sec^{-1}$.

As noted above, the particles in oil are referred to as a pre-mix or concentrate. Optional ingredients which may be used or formed during pre-mix formation are structurants such as soap and emulsifiers. Preferred structurants include soap, such as lauric acid soap. Soaps are generally formed when sodium isethionate and fatty acids are reacted and there is unreacted fatty acid remaining. Soap may be formed from neutralization of the unreacted fatty acid. Preferred emulsifiers include non-ionic surfactants, preferably silicones based non-ionic emulsifier such as Abil® EM 90 from Evonik. Another possible emulsifier is Rheodol® 430V from Kao.

The first step in the process involves preparing FAI in reactor as set forth in step (a) above.

The oil of step (b) is typically a mineral oil. Preferred mineral oil viscosities include 70 SUS (Saybolt Universal Second measure of Kinematic viscosity; calculation of SUS is specified by ASTM, American Society of Testing Materials D2161 specification) and 1000 SUS mineral oils. Assuming viscosities are at the same temperature and that viscosity index is 95 (which is a typical viscosity index for most mineral oils), 70 SUS is roughly equal to about 13.1 centistokes and 1000 SUS is roughly equal to about 216 centistokes. The oils may also be triglyceride oils or silicone oils. Preferred triglyceride oils include soybean oil, sunflower seed oil, canola oil, grapeseed oil, olive oil, palm oil, palm kernel oil, and mixtures thereof; a particularly preferred oil is soybean oil.

Preferably, the oil used is liquid at room temperature. Typically, the melting point of oils used is 30° C. and below, preferably 25° C. and below, more preferably having upper MP range of 10 to 20° C. Preferably, the compositions comprise mineral oil. Preferably, all oils in the composition comprises 25 to 90% of the composition.

In one embodiment, mineral oil comprises 25% to 70% of the composition.

Optional ingredients which may be found in the premix/concentrate include structurants (e.g., soap and/or emulsifier), unreacted fatty acids and unreacted isethionate.

In one embodiment, the composition consists of FAI (including unreacted fatty acids and isethionate as noted) and oil. In another embodiment, the composition consists of FAI, oil and emulsifier. In another embodiment the composition consists of FAI, oil and structurant. The composition may also consist of FAI, oil, structurant, and emulsifier. The oil in any of the above embodiments may be mineral oil or triglyceride or a combination thereof.

In one embodiment, the composition consists of mineral oil, FAI and structurant (e.g., soaps). In one embodiment, the composition consists of mineral oil, FAI, structurant and non-ionic emulsifier, preferably silicone-based non-ionic emulsifier.

In one embodiment, the pre-mix comprises fatty acyl isethionate (e.g., sodium lauroyl isethionate), unreacted fatty acid and soybean oil.

As noted, the various permutations are what we refer to as pre-mix or concentrate. Typically such pre-mix is seen as a "raw ingredient" which can be added with other ingredients to make a "final" oil continuous composition. However, if desired, the premix can be the "final" product and can be commercially sold.

With regard to processing, preferred cooling rates are, as noted, 0.5° to 5° C., preferably 0.5° to 3° C. per minute. If the cooling rate is too high, the pre-mix cannot be successfully formed because solid FAI may precipitate on the walls of the reactor. This results in an inhomogeneous product having a very broad particle size distribution.

Using this controlled cooling, applicants are able to obtain the narrow particle size distribution which characterizes novel compositions made by the novel process of the invention. The particle span of less than 4.5, preferably of 0.1 to 4, preferably 0.1 to 3.

Particle size distributions were measured using a Malvern Mastersizer 3000 laser diffraction instrument fitted with a Small Volume Sample Dispersion Unit. Isopropyl Myristate (IPM, refractive index 1.435) was used as the sample dispersant. A refractive index of 1.485 was used for the dispersed particles. Agitation rate for the Small Sample Dispersion Unit was sufficient to pump dispersant and dispersed sample particles through the measurement chamber, typically 2000 RPM or more.

The sample dispersion unit was cleaned between sample measurements by repeatedly flushing with IPM. For measurement, a few drops of sample were introduced into the dispersion unit, sufficient to produce an obscuration value of less than 20%. (Additional IPM dispersant can be added to further dilute the sample and reduce obscuration below 20%, as needed.) Measurement was started. The measurement protocol employed a 120 second pre-measurement delay to allow complete mixing of the sample in the IPM dispersant. Reported particle size distributions are an average of 3 measurements per sample.

The following parameters are used to characterize the particle size distribution.

D[4,3] is the volume average particle size, also known as the De Brouckere Mean Diameter.

$$D[4,3] = \frac{\sum_{1}^{n} D^4_i v_i}{\sum_{1}^{n} D^3_i v_i}$$

The Di value for each size particle n is the geometric mean diameter. In the numerator, Di to the fourth power is multiplied by the percent of that particle size, summed over all particle sizes. For the denominator, Di to the third power is multiplied by Vi, the percent of that particle size, summed over all particle sizes.

The span is a measure of the polydispersity. It is defined as:

$$\text{Span} = \frac{D[v, 0.9] - D[v, 0.1]}{D[v, 0.5]}$$

The volume median diameter D(v,0.5) is the diameter where 50% of the distribution is above and 50% is below.

D(v,0.9), 90% of the volume distribution is below this value.

D(v,0.1), 10% of the volume distribution is below this value.

The span is the width of the distribution based on the 10%, 50% and 90% quantile.

According to our invention, particle span (as defined above) is less than 4.5.

EXAMPLES

The following examples were made using the process above with M1000 mineral oil as continuous phase.

|  | Example 1 | Example 2 | Example 3 | Example A Comparative |
|---|---|---|---|---|
| Mineral oil | 50 | 50 | 50 | 50 |
| Sodium lauroyl isethionate (FAI) | 37.10 | 39.67 | 37.83 | 31.72 |
| Unreacted free fatty acid | 8.66 | 6.33 | 9.41 | 2.54 |
| Unreacted sodium isethionate, zinc oxide catalyst, and trace impurities, if any | Balance | Balance | Balance | Balance |
| Cooling rate | 2.0° C./min. | 2.0° C./min. | 2.0° C./min. | Uneven throughout the reactor and ranging from 1.4 to 8.4° C./min. |
| D 4,3 | 43.46 | 40.73 | 54.38 | 50.87 |
| Span | 2.57 | 2.08 | 2.30 | 8.89 |

All composition amounts are percent by weight.

As seen above, by cooling at the rate of 2° C./minute we were able to obtain small average particle size fatty isethionate particles.

When the rate was uneven throughout the reactor and the difference in rates exceeded 3° C. at different points in the reactor (Example A), the span (8.89) was nearly 3 times as great as other examples. When rate was above 5° C. (both in Example A and in a separate example made by applicant), we could not even make the pre-mix because FAI (SLI) precipitated in the reactor, resulting in inhomogeneous product.

The following compositions were made using the process above M70 mineral oil as continuous phase.

|  | Example 4 | Example 5 | Example 6 | Example 7 | Example 8 | Example 9 |
|---|---|---|---|---|---|---|
| Mineral oil | 50 | 50 | 50 | 50 | 50 | 50 |
| Sodium lauroyl | 39.05 | 36.01 | 40.54 | 37.76 | 37.76 | 36.65 |

-continued

|  | Example 4 | Example 5 | Example 6 | Example 7 | Example 8 | Example 9 |
|---|---|---|---|---|---|---|
| isethionate (FAI) |  |  |  |  |  |  |
| Unreacted Free fatty acid | 6.62 | 10.99 | 6.97 | 8.91 | 8.91 | 9.08 |
| Unreacted sodium isethionate, zinc oxide catalyst, and trace impurities, if any | Balance | Balance | Balance | Balance | Balance | Balance |
| Cooling rate | 1.15° C./min. | 0.67° C./min. | 0.64° C./min. | 0.71° C./min. | 0.71° C./min. | 0.75° C./min. |
| Nonionic emulsifier | — | — | — | — | 0.5% | — |
| D 4, 3 | 11.88 | 91.61 | 42.33 | 61.73 | 63.77 | 77.84 |
| Span | 4.05 | 1.61 | 3.17 | 2.31 | 2.28 | 1.96 |

All composition amounts are percent by weight.

As seen from examples above, the process of the invention results in material where volume average particle size is 100 μm or below and span is 4.5 or below.

Natural triglyceride oil as continuous phase: the following compositions were prepared at bench scale using SLI made by the process previously described. The SLI was melted and heated to a temperature of 220° C. Oil was heated to 120° C. and added to the mixture with agitation. The mixture was reheated to 220° C., then cooled with agitation at 1.0° C./min to a discharge temperature of 70° C.

|  | Example 10 | Example 11 | Example 12 | Example 13 |
|---|---|---|---|---|
| Glycine Soja Soybean Oil | 55 | 55 |  |  |
| Plenish ® Soybean Oil (made by Dupont) |  |  | 55 | 55 |
| Sodium lauroyl isethionate (FAI) | 34.61 | 35.26 | 35.01 | 34.84 |
| Unreacted Free fatty acid | 7.15 | 7.31 | 7.27 | 7.23 |
| Unreacted sodium isethionate, zinc oxide catalyst, and trace impurities, if any | Balance | Balance | Balance | Balance |
| Cooling rate | 1.00° C./min. | 1.00° C./min. | 1.00° C./min. | 1.00 C./min. |
| Nonionic emulsifier | — | 0.5% | — | 0.5% |
| D 4,3 | 24.31 | 24.58 | 34.90 | 31.24 |
| Span | 2.10 | 2.10 | 2.12 | 2.24 |

All composition amounts are percent by weight. Plenish Soybean Oil is a high-oleic soybean oil developed for cooking and other high temperature application.

Examples 14-18 Demonstrating pH of Compositions of Invention

In Examples 14-18, applicants formed five separate 1:1 mixtures of sodium lauroyl isethionate (a sodium alkanoyl isethionate) to mineral oil. pH values for 1% dispersions for each of these mixtures is set forth below:

| Example | pH |
|---|---|
| 14 | 5.7 |
| 15 | 5.23 |
| 16 | 5.56 |
| 17 | 5.55 |
| 18 | 5.48 |

While not wishing to be bound by theory, the pH values are believed to explain why fatty acid soap crystals are not found in compositions of the invention.

Comparative Examples Made by Wet-Milling

50% solids in M70 mineral oil; Example C is 1 pass, Example D is 3 passes and Example E is 5 passes, all through a 3 stage high shear rotor/stator Kinematica Megatron homogenizer @ 9,600 RPM

|  | C | D | E |
|---|---|---|---|
| Mineral oil | 50 | 50 | 50 |
| Sodium lauroyl isethionate (FAI) | 38.67 | 38.67 | 38.67 |
| Unreacted free fatty acid | 6.12 | 6.12 | 6.12 |
| Unreacted sodium isethionate, zinc oxide catalyst, and trace impurities, if any | Balance | Balance | Balance |
| D 4,3 | 40.52 | 30.25 | 30.47 |
| Span | 8.96 | 7.47 | 6.68 |

Although wet milling provides a good volume average particle size below 100 microns, the span is very high, indicating a broad distribution which includes both large particles that contribute to grit and small particles that contribute to a high viscosity.

The invention claimed is:

1. A process for making an oil continuous composition, the process comprising the steps of:
    a) reacting HOR'SO$_3$M,
        where R' is a divalent hydrocarbon radical having 2 to 4 carbons and M is an alkali metal cation,
        with RCOOH, where R is a monovalent aliphatic radical having 7 to 24 carbons to produce RCOOR"SO$_3$M, said reactants being combined at a temperature of 20 to 25° C. and heated to 200° to 245° C.;

b) adding an oil selected from the group consisting of mineral oil, triglyceride oil, silicone oil and mixtures thereof, wherein said oil has optionally been heated from 20-25° C. to 80 to 130° C., to the heated reaction product of step (a) while still in a molten state;

c) continuing to heat a mixture of the product of (a) and oil of (b) at a temperature of 200 to 245° C. to form a liquid phase mixture of fatty acyl isethionate, unreacted fatty acid, unreacted isethionate, catalyst, if used, trace impurities, if any, and oil; and d) cooling the resultant mixture at 0.5 to 5° C. per minute to below the solidification temperature of the fatty acyl isethionate.

2. A process according to claim 1 wherein triglyceride oil is added in step (b) and said triglyceride oil is soybean oil.

3. A process according to claim 1 wherein a catalyst is used in step (c).

4. A process according to claim 3 wherein said catalyst is zinc oxide.

5. A process according to claim 1, wherein the process comprises a pH adjustment, to result in a pH of the resulting composition of between 3.0 and 6.5.

6. A process according to claim 1, wherein the shear rate during step c) and/or d) is 10 to 1000 $sec^{-1}$.

7. An oil continuous composition obtainable by the process of claim 1 comprising fatty acyl isethionate particles which are not pre-aggregated having an average particle size of 100 microns or less and a particle size distribution defined by a span of less than 4.5;

said composition being free of fatty acid soap crystals.

8. A composition according to claim 7 comprising fatty acyl isethionate particles having an average particle size less than 75 microns.

9. A composition according to claim 7, wherein the span is less than 4.

10. A composition according to claim 7, wherein the fatty acid isethionate is sodium alkanoyl isethionate.

11. A composition according to claim 7 comprising 25 to 90% by wt. oil and 10 to 60% by wt. fatty acyl isethionate.

12. A composition according to claim 7 wherein said oil continuous composition is a non-aqueous composition.

13. A composition according to claim 7 having pH of 3.0 to 6.5.

14. The composition according to claim 13, wherein the pH is 4.0 to 6.0.

* * * * *